United States Patent [19]

Hannart et al.

[11] Patent Number: 4,828,831

[45] Date of Patent: May 9, 1989

[54] NEW CONJUGATES OF VINBLASTINE AND ITS DERIVATIVES, PROCESS FOR PREPARING THEM AND PHARMACEUTICAL COMPOSITIONS CONTAINING THEM

[75] Inventors: Jean A. A. Hannart, Dion-Valmont; André B. L. Trouet, Winksele; Kandukuri S. B. Rao, Rosières, all of Belgium

[73] Assignee: Omnichem, Belgium

[21] Appl. No.: 940,974

[22] Filed: Dec. 12, 1986

[30] Foreign Application Priority Data

Dec. 16, 1985 [LU] Luxembourg .................... 86212
Jul. 16, 1986 [LU] Luxembourg .................... 86515

[51] Int. Cl.[4] ................... A61K 39/44; C07K 15/14
[52] U.S. Cl. .............................. 424/85.91; 435/68; 435/69; 530/362; 530/363; 530/388; 530/391; 530/807; 530/812; 530/828; 424/85.8
[58] Field of Search ............... 435/68, 69, 70; 424/85; 530/362, 363, 388, 391, 807, 812, 828, 424

[56] References Cited

U.S. PATENT DOCUMENTS

4,388,305 6/1983 Trouet et al. .................... 548/478
4,667,030 5/1987 Cullinan .......................... 530/388 X
4,675,400 6/1987 Cullinan .......................... 530/388 X

FOREIGN PATENT DOCUMENTS

0088695 9/1983 European Pat. Off.
2137210 10/1984 United Kingdom.

OTHER PUBLICATIONS

Selective Cytotoxicity Against Human Tumour Cells by a Vindesine-Monoclonal Antibody Conjugate, by M. J. Embleton et al., Br. J. Cancer (1983) 47, 043–049, pp. 43–49.
Monoclonal Antibodies for Targeted Therapy with Vindesine, by G. F. Rowland et al., B.2 Oncology, vol. 30, pp. 375–379.
Localisation and Toxicity Study of a Vindesine-Anti-CEA Conjugate in Patients with Advanced Cancer, by C. H. J. Ford et al., Br. J. Cancer (1983), 47,035-042, pp. 35–42.
A Vindesine-Anti-CEA Conjugate Cytotoxic for Human Cancer Cells in Vitro, by J. R. Johnson et al., Br. J. Cancer (1981) 44,372, pp. 472–475.
Embleton et al. "Antitumour Reactions of Monoclonal Antibody Against a Human Osteogenic-Sarcoma Cell Line", Br. J. Cancer, vol. 43, pp. 582–587 (1981).
Ritz et al., "A Monoclonal Antibody to Human Acute Lymphoblastic Leukaemia Antigen", Nature, vol. 283, pp. 583–585 (1980).
K. Sikora et al. "Human Monoclonal Antibodies to Lung-Cancer Antigens", Br. J. Cancer, vol. 43, pp. 696–700 (1981).
Ball et al., "Monoclonal Antibodies Reactive with Human Myeloid Leukaemia Cells", Clin. Exp. Immunol., vol. 48, pp. 655–665 (1982).
Masuho, et al. "Interaction of Monoclonal Antibodies with Cell Surface Antigens of Human Ovarian Carcinomas" Cancer Research, vol. 44, pp. 2813–2819 (1984).
Thompson et al., "A Human Breast Tissue-Associated Antigen Detected by a Monoclonal Antibody", J.N.C.I., vol. 70, pp. 409–419 (1983).
Kennett et al., "Hybrid Myelomas Producing Antibodies Against a Human Neuroblastoma Antigen Present on Fetal Brain", Science, vol. 203, pp. 1120–1121 (1979).
Koprowski et al., "Study of Antibodies Against Human Melanoma Produced by Somatic Cell Hybrids" Proc. Natl. Acad. Sci. USA, vol. 75, pp. 3405–3409 (1978).
Thompson et al., "Monoclonal Antibodies to Human Colon and Colorectal Carcinoma", Br. J. Cancer, vol. 47, pp. 595–605 (1983).
Ball, et al., "Monoclonal Antibodies Reactive with Small Cell Carcinoma of the Lung", J.N.C.I., vol. 72, pp. 593–598 (1984).
Conrad, et al., "Structure–Activity Relationships of Dimeric Catharanthus Alkaloids. 2. Experimental Antitumor Activities of N-Substituted Deacetylvinblastine Amide (Vindesine) Sulfates", Jour. of Medicinal Chemistry, vol. 22, pp. 391–400 (1979).
Teale, et al., "Radioimmunoassay of Vinblastine and Vincristine", Br. J. Clin. Pharmac., vol. 4, pp. 169–172 (1977).
Means et al. "Chemical Modification of Proteins", Holden Day Inc., pp. 110–111 (1971).

Primary Examiner—Howard E. Schain
Attorney, Agent, or Firm—Ostrolenk, Faber, Gerb & Soffen

[57] ABSTRACT

A description is given of conjugates of vinca alkaloid of the indole-dihydroindole type with a protein or a protein fragment, corresponding to the general formula

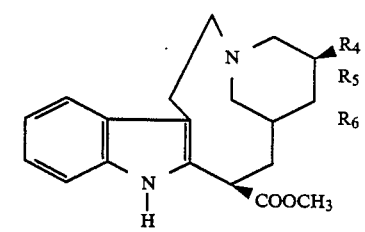

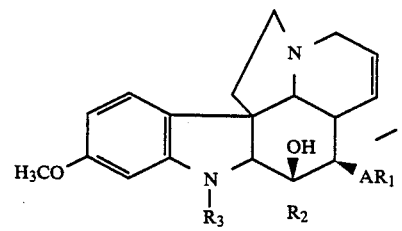

in which
$R_1$ denotes a protein or a protein fragment;
$R_2$ is $COO(C_{1-3}$ alkyl) or $CO-R_7$ where $R_7$ is $NH_2$ or an amino acid ester or peptide ester;
$R_3$ is H, $CH_3$ or CHO;

when $R_5$ and $R_6$ are taken separately, $R_6$ is H and one of $R_4$ and $R_5$ is ethyl and the other is H or OH;

when $R_5$ and $R_6$ are taken together with the carbon atoms to which they are attached, they form an oxirane ring and $R_4$ is ethyl, and A is a residue of a bifunctional organic derivative of the maleoylamino acid or maleoyl peptide or maleoylphenoxy type.

13 Claims, No Drawings

NEW CONJUGATES OF VINBLASTINE AND ITS DERIVATIVES, PROCESS FOR PREPARING THEM AND PHARMACEUTICAL COMPOSITIONS CONTAINING THEM

The present invention relates to new conjugates of vinca alkaloids of the indole-dihydroindole type with proteins or protein fragments which are endowed with pharmaceutical properties, and especially cytostatic activity. Vinca alkaloids of the indole-dihydroindole type, in particular vinblastine, vincristine and vindesine, are used in the treatment of cancer. The chemotherapeutic use of these derivatives is, however, limited in its effectiveness by their side effects. For this reason, many derivatives have been synthesized in order to reduce these side effects.

Vinblastine and some of its derivatives, especially vincristine or vindesine, have already been coupled to proteins, for example albumin or various immunoglobulins. This results in coupling products or compounds known as conjugates.

We note, in particular, the following references in the literature:
- J. D. Teale, Jacqueline M. Clough and V. Marks, Br. J. Clin. Pharmac. 4, 169–172, 1977
- C. H. J. Ford, C. E. Newman, J. R. Johnson, C. S. Woodhouse, T. A. Reeder, G. F. Rowland and R. G. Simmonds, Br. J. Cancer 47, 35–42, 1983
- M. J. Embleton, G. F. Rowland, R. G. Simmonds, E. Jacobs, C. H. Marsden and R. W. Baldwin, Br. J. Cancer 47, 43–49, 1983
- J. R. Johnson, C. H. J. Ford, C. E. Newman, C. S. Woodhouse, G. F. Rowland and R. G. Simmonds, Br. J. Cancer, 44, 472–475, 1981
- Eli Lilly Eur. Pat. Applic., Publ. no. 56,322, 21.07.82
- R. A. Conrad, G. J. Cullinan, K. Gerzon and G. A. Poore, J. Med. Chem. 22, 391, 1979
- Eli Lilly, U.K. Pat. Applic., Publ. no. 2,137,210 03.11.84
- OmniChem, Eur. Pat. Applic., Publ. no. 124,502, 07.11.84.

The coupling of these indole-dihydroindole dimers has been undertaken, not only with the object of developing new immunological reagents, but especially for the purpose of preparing more active antitumor substances which are more selective and less toxic.

Two types of coupling have hitherto been envisaged:
(a) coupling at $C^3$ via an azide derivative (Eur. Pat. Appl., Publ. no. 56,322).
(b) Coupling at $C^4$ via an ester group derived from the hydroxyl group on carbon 4 of the vinca alkaloid skeleton (U.K. Pat. Appl., Publ. no. 2,137,210; Eur. Pat. Appl. no. 124,502).

The present invention relates to new products which are conjugates of vinca alkaloids of the indole-dihydroindole type with proteins or protein fragments, wherein the coupling is also accomplished via an ester group derived from the hydroxyl group on carbon 4 of the vinca alkaloid skeleton.

The subject of the invention consists, more especially, of conjugates of vinca alkaloid of the indoledihydroindole type with a protein or a protein fragment, corresponding to the general formula

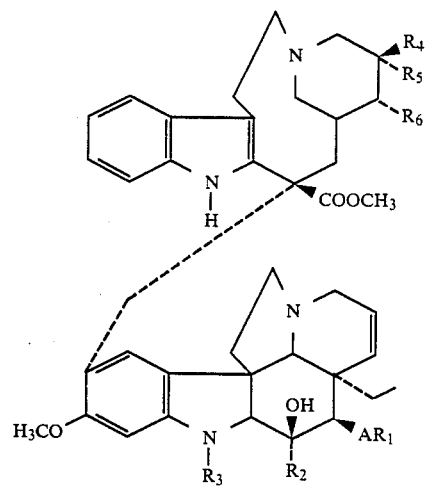

in which
- $R_1$ denotes a protein or a protein fragment;
- $R_2$ is $COO(C_{1-3}$ alkyl$)$ or $CO—R_7$ where $R_7$ is $NH_2$ or an amino acid ester or peptide ester;
- $R_3$ is H, $CH_3$ or CHO;
- when $R_5$ and $R_6$ are taken separately, $R_6$ is H and one of $R_4$ and $R_5$ is ethyl and the other is H or OH;
- when $R_5$ and $R_6$ are taken together with the carbon atoms to which they are attached, they form an oxirane ring and $R_4$ is ethyl, and
- A is a residue of a bifunctional organic derivative of the maleoylamino acid or maleoyl peptide or maleoylphenoxy type.

In these conjugates, according to the invention, the protein or protein fragment is coupled to the vinca compound via an arm, by prior condensation of the 4-deactylindole-dihydroindole vinca alkaloid with a bifunctional organic derivative of the maleoylamino acid type or maleoyl peptide type of general formula

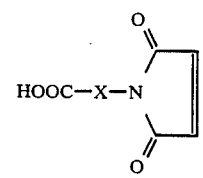

In the case of maleoylamino acids, X denotes
- a linear alkylene chain of 1 to 12 carbon atoms,
- a branched alkylene chain of 2 to 5 carbon atoms,
- a cycloalkylene chain of 3 to 6 carbon atoms, or
- a phenylene chain of 3 to 6 carbon atoms.

In addition, when the bifunctional derivative is of the maleoylamino acid type, X denotes, apart from the meanings stated above, the group R—CH of natural amino acids

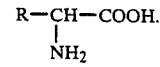

In this latter case, it is self-evident that, when the group R—CH bears functional substituents, the latter can be protected by the protective groups customarily used in peptide synthesis.

In the case of maleoyl peptides, x denotes a fragment of a peptide chain $-(X_1-NH-CO)_n-X_1-$ where $n=1, 2, 3$ or 4 and $X_1$ has the same meaning as X described above.

X can also denote a phenyl radical.

When the bifunctional derivative defined above comprises asymmetric centers, it can be used in its racemic form or in one of its optically active forms.

More especially, the conjugates of the invention can be represented by the following formula:

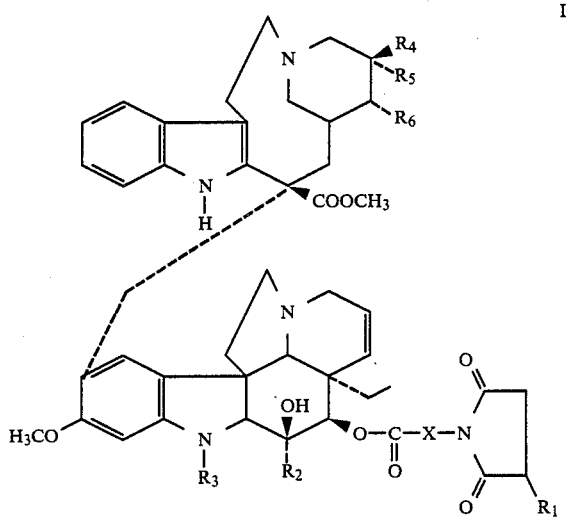

I in which
$R_1$ denotes a protein or a protein fragment,
X is as defined above,
$R_2$ is $COO(C_{1-3}$ alkyl), or $CO-R_7$ where $R_7$ is $NH_2$ or an aminoacid ester or peptide ester,
$R_3$ is H, $CH_3$ or CHO,
when $R_5$ and $R_6$ are taken separately, $R_6$ is H and one of $R_4$ and $R_5$ is ethyl and the other is H or OH, and when $R_5$ and $R_6$ are taken together with the carbon atoms to which they are attached, they form an oxirane ring and $R_4$ is ethyl.

The compounds having the above formula can be described generically as either vinblastine derivatives where $R_2$ is $COOCH_3$, $R_3$ is methyl, $R_4$ is hydroxyl, $R_5$ is ethyl and $R_6$ is hydrogen, vindesine derivatives where $R_2$ is $CO-NH_2$, and $R_3$, $R_4$, $R_5$ and $R_6$ have the meaning stated for the vinblastine derivatives, 23-vinblastinoylamino acid derivatives where $R_2$ is $CO-R_7$, $R_7$ being an amino acid ester or peptide ester, and $R_3$, $R_4$, $R_5$ and $R_6$ have the meaning stated for the vinblastine derivatives, vincristine derivatives where $R_2$ is $COOCH_3$, $R_3$ is formyl, $R_4$ is hydroxyl, $R_5$ is ethyl and $R_6$ is hydrogen, leurosidine derivatives where $R_2$ is $COOCH_3$, $R_3$ is methyl, $R_4$ is ethyl, $R_5$ is hydroxyl and $R_6$ is hydrogen, derivatives of 4-deoxy-VLB "A" where $R_2$ is $COOCH_3$, $R_3$ is methyl, $R_4$ and $R_6$ are hydrogen, and $R_5$ is ethyl, derivatives of 4-deoxy-VLB "B" where $R_2$ is $COOCH_3$, $R_3$ is methyl, $R_4$ is ethyl, and $R_5$ and $R_6$ are hydrogen, and leurosine derivatives where $R_2$ is $COOCH_3$, $R_3$ is methyl, $R_4$ is ethyl, and $R_5$ and $R_6$ together form an epoxide link.

The bifunctional derivative of the maleoylamino acid type can result from the condensation of an N-alkoxymaleimide with an amino acid, natural or otherwise, and in the case of condensation with glycine, $X=CH_2$; with alanine, $X=CH-CH_3$; with β-alanine, $X=(CH_2)_2$; with phenylalanine, $X=CH-CH_2-C_6H_5$; with α-aminobutyric acid, $X=CH-CH_2-CH_3$; with valine, $X=CH-CH-(CH_3)_2$; with norvaline, $X=CH-CH_2-CH_2-CH_3$; with leucine, $X=-CH-CH_2-CH-(CH_3)_2$; with isoleucine,

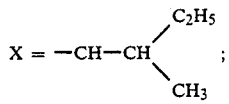

with norleucine, $X=CH-(CH_2)_3-CH_3$; with 6-aminocaproic acid, $X=(CH_2)_5$; with 11-aminoundecanoic acid, $X=(CH_2)_{10}$; and with 12-aminododecanoic acid, $X=(CH_2)_{11}$.

The bifunctional derivative of the maleoyl peptide type can also result from the condensation of an N-alkoxymaleimide with a dipeptide or tripeptide, to give a derivative $-(X_1-NH-CO-)_nX_1$ where $X_1$ can have the same meaning as X described above.

The proteins which can advantageously be used are, in particular, bovine or human serum albumin, or fetuin or immunoglobulins.

The proteins used can also be treated in order to be selectively modified. These modifications enable protein conjugates to be obtained which, when they are used therapeutically, will be preferentially concentrated in certain tissues, for example in the liver. It is thus possible, prior to the condensation of the vinca alkaloid derivative with the protein, to galactosylate the latter.

The immunoglobulins specific for malignant cell surface antigens, and the techniques for producing them from serum of immunized animals or by culturing hybridomas which secrete monoclonal antibodies, are well known. The preferred type of antibody for use in the invention is an immunoglobulin of the IgG class of human origin.

However, the immunoglobulins of other species are also included in this invention. Some representative immunoglobulins are as follows:

Ig of goat or sheep immunized with carcinoembryonic antigen;
rabbit anti-LLA Ig;
various monkey anti-LLA, anti-LMA, anti-LLC, anti-LMC Ig's;
Ig of goat or sheep immunized with membranes of carcinoma of the lung;
monoclonal Ig from mouse hybridomas secreting antibodies against human colorectal carcinoma;
monoclonal Ig from mouse hybridomas secreting antibodies against human melanoma;
monoclonal Ig from mouse hybridomas secreting antibodies which react with human leukemia cells;
monoclonal Ig from mouse hybridomas secreting antibodies which react with human neuroblastoma cells;
monoclonal Ig from mouse hybridomas secreting antibodies which react with human breast cancer antigens;
monoclonal Ig from mouse hybridomas secreting antibodies which react with human ovarian carcinoma cells; p1 monoclonal Ig from mouse hybridomas secreting antibodies which react with human osteosarcoma cells; and monoclonal Ig from mouse hybridomas secreting antibodies to lung cancer.

The conjugates can also be prepared with immunoglobulin fragments, namely Fab, Fab' or F(ab')$_2$ fragments or monomeric IgM, obtained from an antibody by digestion with a proteolytic enzyme.

The conjugates of the present invention are obtained, in a first stage, by esterification of a maleoylamino acid or a maleoyl peptide with the C$^4$-hydroxyl of a 4-deacetylindole-dihydroindole vinca alkaloid of formula II, to give a derivative of formula III, G. E. and Feeney, R. E.; Chemical modification of proteins, 1971, p. 110–138, Holden Day Inc., San Francisco) to give the conjugates I.

From the chemical standpoint:

the production of the maleoylamino acids or maleoyl peptides is carried out according to the methods described by O. Keller and J. Rudinger, Helv. 58, 531 (1975), by D. H. Rich, P. D. Gesselchen, A. Tong, A. Cheung and C. K. Buckner, J. Med. Chem, 18, 1004 (1975) and by A. Sato and M. Nakao, J. Biochem., 90, 1117 (1981).

The condensation of the maleoyl derivatives with the vinca alkaloid can be performed in the conventional

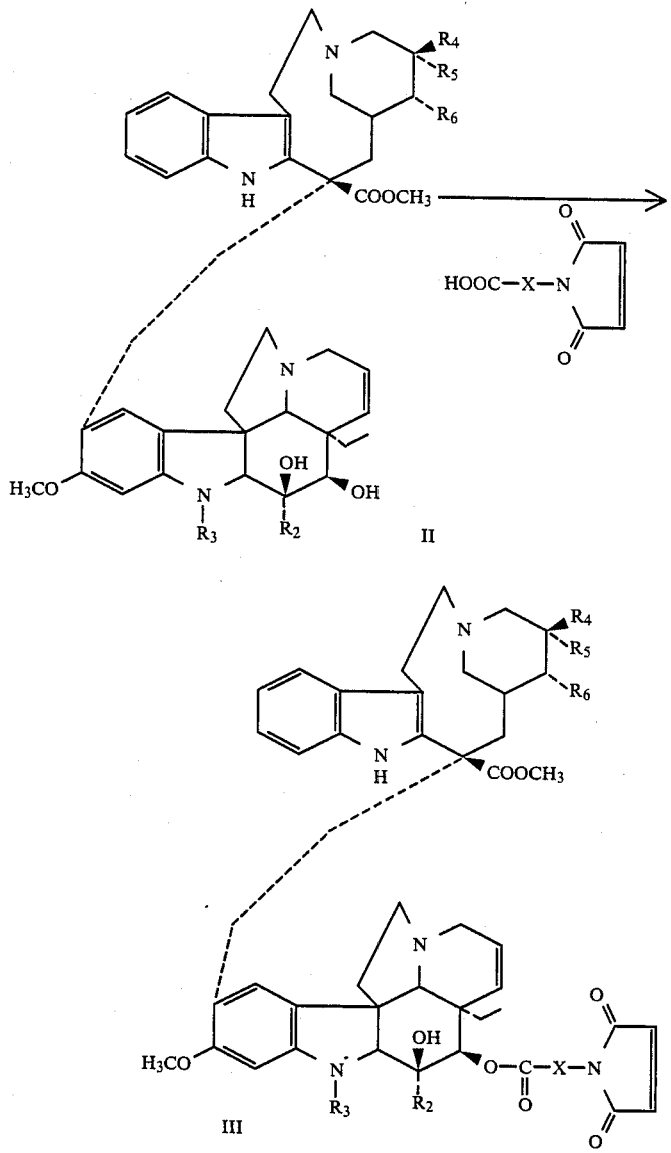

in which X, R$_2$, R$_3$, R$_4$, R$_5$ and R$_6$ have the meaning stated above.

In a second stage, the 4-carboxy-maleoyl vinca derivatives III are then condensed with a protein or a protein fragment by addition of either the free thiol groups or the free amino groups of the protein, for example the amino groups derived from lysine residues of the protein, to the olefinic double bond of the maleimide, according to a Michael type addition mechanism (Means, manner with an alkyl chloroformate, preferably ethyl or isobutyl chloroformate, in the presence of an amine base such as triethylamine, N-methylpiperidine or N-methylmorpholine, in an organic solvent such as ethyl acetate, tetrahydrofuran or methylene chloride.

The derivative obtained is isolated from the reaction medium and purified by means of classical methods used in chemistry.

Any other method of activation of the carboxyl group of the maleoylamino acid or maleoyl peptide for carrying out the condensation with the vinca alkaloid, especially the methods used in peptide chemistry, can be applied to this type of condensation.

In particular, in the case where X is phenyl, the condensation is carried out with N-succinimidyl 3-maleimidobenzoate, obtained according to the methods described by T. Alkawa, J. Biochem., 79, 233 (1976) and M. J. O'Sullivan et al., Anal. Biochem., 100, 100 (1979).

The production of the conjugates can be carried out by reacting the protein, the polyclonal or monoclonal antibody, with the vinca compound of formula III under classical conditions, for example in aqueous medium at a temperature of between 4° C. and 40° C. and a pH of 7.5 to 9.5.

The numbers of residues attached can depend on the concentration of the reagents and the reaction time, but the average number is generally between 5 and 20.

For example, a solution of the compound III in an organic solvent such as dioxane is added dropwise to a buffered solution of protein, for example in 0.1M phosphate buffer at pH 8.2. After the mixture is left overnight at room temperature, the conjugate is isolated by gel filtration, concentrated by ultrafiltration and sterilized. The protein content is measured by the Lowry method and the alkaloid content estimated by measuring the radioactivity.

The "in vitro" and "in vivo" trials performed with the compounds of the invention to demonstrate their antitumor activity show that the formation of the conjugate via a maleoyl link

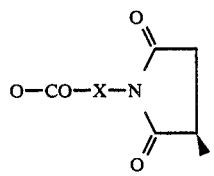

can be more advantageous than with a O—CO—X—CO— link.

In effect, the maleoyl link makes it possible to conjugate both the free amino groups and thiol groups of the protein or protein fragment. In addition, digestion with lysosomal enzymes indicates that the vinca alkaloid is liberated to a much greater extent in the case of the maleoyl link. The conjugates are also stable in serum and at acid pH.

The compounds of the invention were tested on $BDF_1$ mice in which a P388 leukemia had been implanted intraperitoneally. The first results indicate that the compounds show significant activity on this experimental model since they induce an increase in the survival time.

The new conjugates of the invention show antitumor properties which are especially advantageous and capable of being used in human therapy.

For their application in therapy, the compounds of the invention are preferably administered parenterally, dissolved in a pharmaceutically acceptable solvent. Physiological saline or other solutions buffered, for example, with a phosphate are suitable solvents. The active substance is generally administered at a dosage which can vary from 50 mg to several grams.

The compounds of the invention can, in addition, be used in combination with other antitumor agents.

The examples which follow illustrate without implied limitation the process which leads to the compounds of the invention.

EXAMPLE 1

N-carbomethoxymaleimide

A solution of 3.8 g (0.04 mol) and 4 g (0.04 mol) of triethylamine in 150 ml of ethyl acetate is treated at 0° C. with 3 ml (0.04 mol) of methyl chloroformate dissolved in 20 ml of ethyl acetate. After 1 hour's stirring, the precipitate is filtered off and washed with ethyl acetate. The organic phases are combined, washed with water, dried over anhydrous sodium sulfate and evaporated to dryness under vacuum.

The residue, crystallized in an ethyl acetate/isopropyl ether mixture, gives 4.19 g of N-carbomethoxymaleimide.

NMR spectrum: ($CDCl_3$, $\delta$), 6.75 (2H, s), 3.9 (3H, s).

EXAMPLE 2

N-maleoyl-L-alanine

A solution of 2.3 g (0.025 mol) of L-alanine in 100 ml of saturated sodium bicarbonate solution is treated at 0° C., with vigorous stirring, with 3.7 g (0.025 mol) of N-carbomethoxymaleimide.

After one hour, the solution is diluted with 200 ml of water and stirred at 40° C. for 1 hour. The pH of the solution (8.2) is then brought to 6.4 by adding concentrated surfuric acid. The solution is then concentrated to 100 ml and acidified to pH 2 by adding 1M sulfuric acid, and is extracted three times with ethyl acetate. The organic phases are combined, dried over anhydrous sodium sulfate and evaporated to dryness under vacuum.

The residue obtained is purified by chromatography on a silica column (elution: chloroform/acetic acid, 95:5). 1.2 g of N-maleoyl-L-alanine is obtained in this manner.

Yield: 48%.

IR spectrum (KBr) $cm^{-1}$: 3400, 3100, 2930, 1780, 1740, 1700, 1460, 1420, 1390, 1370, 1345, 1220, 1175, 1118, 1080, 1068, 1015, 970, 835, 700.

NMR spectrum ($CDCl_3$, $\delta$): 6.7 (2H, s); 4.8 (1H, g); 1.65 (3H, d).

EXAMPLE 3

N-maleoyl-6-aminocaproic acid

A solution of 4.2 g (32.3 mmol) of 6-aminocaproic acid in 163 ml of saturated sodium bicarbonate solution is treated at 0° C., with vigorous stirring, with 5 g (32.3 mmol) of N-carbomethoxymaleimide. After 1 hour, the solution is diluted with 256 ml of water and stirred at room temperature for 1 hour. The pH of the solution (8.2) is then brought to 6.4 by adding concentrated sulfuric acid. The solution is then concentrated to 100 ml and acidified to pH 2 by adding 1M sulfuric acid, and is extracted three times with ethyl acetate. The organic phases are combined, dried over anhydrous sodium sulfate and evaporated to dryness under vacuum. The residue is purified by chromatography on a silica column (elution: chloroform/acetic acid, 95:5). In this manner, 4.7 g of N-maleoyl-6-aminocaproic acid are obtained.

Yield: 51%.

IR spectrum (KBr/$cm^{-1}$): 3,090; 2,940; 2,880; 1,770; 1,710; 1,470; 1,450; 1,380; 1,370; 1,340; 1,315; 1,260;

1,210; 1,135; 1,110; 1,140; 1,100; 1,015; 1,000; 815; 840; 735; 700.

EXAMPLE 4

N-maleoyl-L-glutamic acid γ-methyl ester

A solution of 1 g (6.2 mmol) of L-glutamic acid γ-methyl ester in 31.2 ml of saturated sodium bicarbonate solution is treated at 0° C., with vigorous stirring, with 961 mg (6.2 mmol) of N-carbomethoxymaleimide. After 1 hour, the solution is diluted with 126 ml of water and stirred at 40° C. for one hour. The pH of the solution (8.2) is then brought to 6.4 by adding concentrated sulfuric acid. The solution is then concentrated to 50 ml and acidified to pH 2 by adding 1M sulfuric acid, and is extracted three times with ethyl acetate. The organic phases are combined, dried over anhydrous sodium sulfate and evaporated to dryness under vacuum. The residue obtained is purified by chromatography on a silica column (elution: chloroform/acetic acid, 95:5). In this manner, 956 mg of pure product are obtained.

Yield: 49%.

NMR spectrum 60: 7.9 (s, acid H); 6.5 (s, maleimide); 4.6 (m, CH*); 3.5 (s, OCH$_3$); 2.3 (m, glu CH$_2$), IR spectrum (KBr) cm$^{-1}$: 3,470, 3,110, 2,960, 2,600, 1,775, 1,750–1,690, 1,440, 1,410, 1,265–1.150, 1,090, 1,015, 830, 700.

EXAMPLE 5

N-maleoyl-L-isoleucine

Following the procedure of Example 2, N-maleoyl-L-isoleucine is obtained by treating 424 mg (3.22 mol) of L-isoleucine with 500 mg (3.2 mmol) of N-carbomethoxymaleimide.

YLd: 20%,

Mass spectrum (CDI, isobutane): 423 (2M+1), 352, 270, 212 (M+ +1), 188, 166, 132, 123.

NMR spectrum (CDCl$_3$,): 8.55 (should, OH); 6.85 (2, s, maleimide double bond); 4.65 (1, d, C*H); 2.6 (m, 1, CH); 1.28 (d, CH$_3$); 1.1 (m, CH$_3$).

EXAMPLE 6

N-maleoyl-L-aspartic acid α-benzyl ester

A solution of 1 g (4.48 mmol) of N-maleoyl-L-aspartic acid α-benzyl ester in 22.5 ml of saturated sodium bicarbonate solution is treated at 0° C., with vigorous stirring, with 694 mg (4.48 mmol) of N-carbomethoxymaleimide.

After 1 h, the solution is diluted with 91 ml of water and stirred at 40° C. for one hour. The pH of the solution (8.2) is then brought to 6.4 by adding concentrated sulfuric acid. The solution is then concentrated to 50 ml and acidified to pH 2 by adding 1M sulfuric acid, and is extracted three times with ethyl acetate.

The organic phases are combined, dried over anhydrous sodium sulfate and evaporated to dryness under vacuum.

The residue obtained is purified by chromatography on a silica column (elution: chloroform/acetic acid, 95:5). In this manner, 267 mg of pure product are obtained.

Yield: 20%, 7.1 (5H, m, benzyl H); 6.6 (2H, s, maleimide db); 5 (2H, s, benzyl CH$_2$ 3.1 (2H, m, CH$_2$).

NMR spectrum (CD$_3$OD, 60 MHz, ppm):

IR spectrum (KBr, cm$^{-1}$): 3060, 1765, 1745, 1720, 1410, 1270, 830, 740, 750.

EXAMPLE 7

N-maleoyl-11-aminoundecanoic acid

A solution of maleic anhydride (2.4 g; 24.8 mmol) in 10.1 ml of acetic acid is added to a solution of 11-aminoundecanoic acid (5 g; 24.8 mmol) in 30 ml of acetic acid, and the mixture is maintained with vigorous stirring at room temperature for 3 hours.

The white precipitate is filtered off, washed with cold acetic acid and dried (6.3 g; 21.1 mmol; 85%). 3 g of the precipitate (10.00 mmol) are dissolved in dry toluene (300 ml) and treated with triethylamine (2 g; 22.2 mmol).

The solution is brought to reflux in a Dean and Stark apparatus with vigorous stirring, until the toluene has evaporated. The product is purified on a silica column (elution chloroform/acetic acid: 95:5). In this manner, 1.06 g of N-maleoyl-11-aminoundecanoic acid is obtained.

Yield: 37%,

NMR spectrum (60 MHz, CDCl$_3$, ppm): 8.8 (bp, COOH); 6.5 (2H, s, maleimide db); 3.4 (2H, m, CH$_2$); 2.3 (2H, m, CH$_2$); 1.2 (16H, bp, 8CH$_2$).

IR spectrum (KBr, cm$^{-1}$): 3450, 3100, 2910, 2850, 1770, 1700, 1610, 1590, 1470, 1450, 1420, 1375, 1340, 1310, 1280, 1240, 1180, 1125, 840, 700.

EXAMPLE 8

N-maleoyl-12-aminododecanoic acid

A solution of maleic anhydride (2.28 g; 23.22 mmol) in 9.6 ml of acetic acid is added to a solution of 12-aminododecanoic acid (5 g; 23.22 mmol) in 28 ml of acetic acid, and the mixture is maintained with vigorous stirring at room temperature for 3 hours.

The white precipitate is filtered off, washed with cold acetic acid and dried (6.2 g, 20.9 mmol, 86%). 4.9 g of the precipitate (15.9 mmol) are dissolved in dry toluene (500 ml) and treated with triethylamine (4.9 ml, 35 min). The solution is brought to reflux in a Dean and Stark apparatus with vigorous stirring, until the toluene has evaporated. The product is purified on a silica column (elution: chloroform/acetic acid, 95:5). In this manner, 1.38 g of N-maleoyl-12-aminododecanoic acid is obtained.

Yield: 29%,

NMR spectrum (60 MHz, CDCl$_3$, ppm): 6.52 (2H, s, maleimide db); 3.42 (2H, m, CH$_2$); 2.3 (2H, m, CH$_2$); 1.25 (18H, broad peak, 9—CH$_2$—).

IR spectrum (KBr, cm$^{-1}$): 3450, 3080, 2920, 2825, 1770, 1470, 1450, 1440, 1415, 1380, 1340, 1300, 1260, 1250, 1205, 1120, 920, 840, 700.

EXAMPLE 9

4-(N-maleoyl-L-alanyl)vinblastine

A solution of 1.17 ml (0.009 mol) of isobutyl chloroformate in 5 ml of ethyl acetate is added dropwise to a solution of 1.52 g (0.009 mol) of N-maleoylalanine and 1.25 ml (0.009 mol) of triethylamine in 10 ml of ethyl acetate cooled to 0° C. The mixture is stirred for 1 h 30 min at 0° C., and 2.3 g (0.003 mol) of O$^4$-deacetylvinblastine dissolved in 20 ml of ethyl acetate are added while the temperature is kept at 0° C. The mixture is then allowed to return to room temperature and is stirred for 10 hours. 50 ml of ethyl acetate and 50 ml of 10% strength aqueous sodium carbonate solution are added. The mixture is stirred and the organic phase decanted and separated. The aqueous phase is extracted three times with ethyl acetate. The combined organic phases are washed with an aqueous solution, dried over magnesium sulfate and evaporated to dryness under vacuum. The residue obtained is purified by chromatography on a silica column (elution: dichloromethane/methanol, 92:8). 1.86 g of pure product is thereby obtained.

Yield: 67.6%,

Mass spectrum (DCI, isobutane): 935 (M+14), 922 (M+1), 921 (M), 751, 693, 519, 445, 371, 133.

NMR spectrum (CDCl$_3$, 360 MHz, ppm): 8 (NH, 1H); 7.5–7 (4H, H—9', H—10', H—11', H—12'); 6.7 (2H, anhydride); 6.55 (1H, H—14); 6.05 (1H, H—17); 5.85 (1H, H—7); 5.45 (1H, H—4); 5.15 (1H, H—6); 4.8 (1H, CH$^x$); 3.95 (1H, H—17'); 3.85 (3H, —OMe); 3.78 (3H, —OMe); 3.7 (1H, H—2); 3.6 (3H, —OMe); 2.7 (3H, NMe); 1.72 (3H, alanine CH$_3$); 0,9–0,8 (6H, CH$_3$—21, CH$_3$—21').

EXAMPLE 10

4-(N-maleoyl-6-aminocaproyl)vinblastine

A solution of 371 μl (2.861 mmol) of isobutyl chloroformate in 1 ml of ethyl acetate is added dropwise to a solution of 604 mg (2.861 mmol) of N-maleoyl-6-aminocaproic acid and 514 μl (4.65 mmol) of N-methylmorpholine in 4 ml of ethyl acetate cooled to 0° C. The mixture is stirred for 3 minutes at 0° C., and 550 mg (0.715 mmol) of O$^4$-deacetylvinblastine dissolved in 1 ml of ethyl acetate is then added while the temperature is kept at 0° C. The mixture is then allowed to return to room temperature and is stirred for 10 hours. The solution is filtered and the ethyl acetate phase evaporated to dryness under vacuum. The residue obtained is purified by chromatography on a silica column (elution: dichloromethane/methanol, 96:4). 263 mg of pure product are thereby obtained.

Yield: 23%,

Mass spectrum (DCI, isobutane): 993; 979; 965 (M$^+$+4); 963 (M$^+$+2); 961 (M$^+$); 946; 933; 920; 906; 812; 754; 693.

IR spectrum (KBr, cm$^{-1}$): 3,400; 3,050; 2,940; 1,740; 1,700; 1,615; 1,500; 1,460; 1,440; 1,410; 1,370; 1,220; 1,170; 1,040.

NMR spectrum (CDCl$_3$, 360 MHz, ppm): 7.47–7,12 (4H, m, H$^{11'}$, H$^{12'}$, H$^{13'}$, H$^{14'}$); 6.65 (2H, s, maleimide db); 6.55 (14, s, H$^{14}$); 6.05 (1H, s, H$^{17}$); 5.82 (1H, m, H$^7$); 5.42 (1H, s, H$^4$); 5.25 (1H, m, H$^6$); 3.92 (1H, m, H$^{17'}$); 3.77 (6H, s, OCH$_3$, C$^{23}$OOCH$_3$); 3.70 (1H, s, H$^2$); 3.6 (3H, s, C$^{18'}$OOCH$_3$); 2.7 (3H, s, NCH$_3$); 2.32 (m, aminocaproic CH$_2$); 1.62 (m, aminocaproic CH$_2$); 0.9–0.8 (6H, t, CH$_3$—21+CH$_3$—21').

EXAMPLE 11

4-(N-maleoyl-L-glutamyl)vinblastine γ-methyl ester

A solution of 152 μl (1.170 mmol) of isobutyl chloroformate in 1 ml of ethyl acetate is added dropwise to a solution of 282 mg (1.170 mmol) of N-maleoyl-L-glutamic acid γ-methyl ester and 163 μl (1.170 mmol) of triethylamine in 1.4 ml of ethyl acetate cooled to 0° C. The mixture is stirred for 4 min at 0° C., and 300 mg (0.390 mmol) of O$^4$-deactylvinblastine dissolved in 1 ml of ethyl acetate are then added while the temperature is kept at 0° C. The mixture is then allowed to return to room temperature and is stirred for 10 hours. The solution is filtered and the organic phase concentrated under vacuum. The residue obtained is purified by chromatography on a silica column (elution: ethanol/ethyl acetate, 30:90). 222 mg of pure product are thereby obtained.

Yield: 38%,

Mass spectrum (DCI, isobutane): 1,036, 1,022, 1,009, 995 (M$^+$+4), 992 (M$^+$+1), 937, 885, 811, 751, 694, 635, 541.

NMR spectrum (CDCl$_3$, 360 MHz, ppm): 9.4 (1H, m, OH); 8 (1H, s, ind NH); 7.5–7.10 (4H, m, H$^{11'}$, H$^{12'}$, H$^{13'}$, H$^{14'}$); 6.7 (2H, s, maleimide db); 6.58 (1H, s, H$^{14}$); 6.05 (1H, s, H$^{17}$); 5.80 (1H, m, H$^7$); 5.48 (1H, s, H$^4$); 5.25 (1H, m, H$^6$); 4.73 (1H, m, Glu CH*); 3.95 (1H, m, H$^{17'}$); 3.85 (3H, s, ar OCH$_3$); 3.75 (3H, s, C$^{23}$OOCH$_3$); 3.63 (3H, s, C$^{18'}$OOCH$_3$); 3.58 (3H, s, Glu OCH$_3$); 2.80 (3H, s, NCH$_3$); 2.38 (m, Glu CH$_2$); 0.9–0.8 (6H, t, CH$_3^{21}$+CH$_3^{21'}$).

IR spectrum (KBr) cm$^{-1}$: 3,430, 1,740, 1,715, 1,615, 1,500, 1,460, 1,430, 1,405, 1,385, 1,250, 1,225, 1,030, 1,005, 825.

EXAMPLE 12

4-(N-maleoyl-N-isoleucyl)vinblastine

A solution of 92 μl (0.7109 mmol) of isobutyl chloroformate in 1 ml of ethyl acetate is added dropwise to a solution of 150 mg (0.7109 mmol) of N-maleoyl-L-isoleucine and 99 μl (0.7109 mmol) of triethylamine in 1 ml of ethyl acetate cooled to 0° C. The mixture is stirred for 3 min at 0° C., and 182 mg (0.237 mmol) of O$^4$-deacetylvinblastine dissolved in 1 ml of ethyl acetate is then added while the temperature is kept at 0° C. The mixture is then allowed to return to room temperature and is stirred for 10 hours. The solution is filtered and the ethyl acetate phase evaporated to dryness under vacuum. The residue obtained is purified by chromatography on a silica column (elution: ethanol/ethyl acetate, 30:90). 133 mg of pure product are thereby obtained.

Yld.: 40%.

Mass spectrum (DCI, acetone): 1,039; 963 (M$^+$+2); 904; 812; 769; 728; 637; 593; 549.

IR spectrum (KBr, cm$^{-1}$): 3,480–3,400; 2,960; 2,920; 2,880; 1,775; 1,740; 1,710; 1,610; 1,500; 1,460; 1,430; 1,380; 1,250; 1,200; 1,040; 1,000; 830; 740.

NMR spectrum (CDCl$_3$, 360 mHz, ppm): 9.4 (m, OH); 7.5–7.1 (4H, m, arom. CH 11'-12'-13'-14'); 6.65 (2H, s, d, maleimide d. bond); 6.6 (1H, s, C$^{14}$—H); 6.05 (1H, s, C$^{17}$—H); 5.8 (1H, s, C$^7$—H); 5.45 (1H, s, C$^4$—H); 5.25 (1H, m, C$^6$—H); 4.5 (1H, d, C—H); 3.95 (1H, m, H$^{17'}$); 3.8 (3H, s, OCH$_3$ ar); 3.75 (3H, s, C$^{23}$OOCH$_3$); 3.7 (1H, s, H$^2$); 3.6 (3H, s, C$^{18'}$OOCH$_3$); 2.65 (3H, s, NCH$_3$); 1.1 (d, 3H, isoleucine CH$_3$); 0.9–0.8 (9H, m, isoleucine CH$_3$+CH$_3$—21'+CH$_3$—21).

EXAMPLE 13

4-(N-maleoyl-L-aspartyl)vinblastine α-benzyl ester

A solution of 114 μl (0.88 mmol) of isobutyl chloroformate in 1 ml of ethyl acetate is added dropwise to a solution of 267 mg (0.88 mmol) of N-maleoyl-L-aspartic acid α-benzyl ester and 118 μl (0.88 mmol) of triethylamine in 1 ml of ethyl acetate cooled to 0° C.

The mixture is stirred for 4 minutes at 0° C., and 227 mg (0.29 mmol) of O$^4$-deacetylvinblastine dissolved in 1 ml of ethyl acetate are then added while the temperature is kept at 0° C. The mixture is then allowed to return to room temperature and is stirred overnight.

The solution is filtered and the organic phase concentrated under vacuum. The residue obtained is purified by chromatography on a silica column (elution: ethanol- /ethyl acetate, 30:90). 105 mg of pure product are thereby obtained.

Yield: 34%,

NMR spectrum (CDCl$_3$, 360 MHz, ppm): 8.05 (1H, s, ind $^{16'}$NH); 7.5–7.17 (4H, m, H$^{11'}$H$^{12'}$H$^{13'}$H$^{14'}$); 7.37–7.3 (5H, m, benzyl H); 6.75 (2H, s, maleimide db); 6.60 (1H, s, H$^{14}$); 6.10 (1H, s, H$^{17}$); 5.87 (1H, m, H$^7$); 5.45 (1H, s, H$^4$); 5.30 (1H, m, H$^6$); 5.20 (2H, m, benzyl CH$_2$); 3.95 (1H, m, H$^{17'}$); 3.82–3.75 (6H, s, OCH$_3$+COOCH$_3$$^{23}$); 3.70 (1H, s, H$_2$); 3.62 (3H, s, C$^{18'}$OOCH$_3$); 2.60 (3H, s, NCH$_3$); 0.9–0.8 (6H, t, CH$_3$−21+CH$_3$−21′).

IR spectrum (KBr, cm$^{-1}$) 3460, 3030, 2960, 2880, 1770, 1740, 1715, 1610, 1500, 1460, 1430, 1410, 1380, 1260, 1220, 1175, 1110, 1025, 910, 800, 730, 700.

Mass spectrum (DCI, isobutane): 1085, 1071, 1057, 1054, 1039, 1023, 1013, 768, 708, 542, 158.

EXAMPLE 14

4-(N-maleoyl-11-aminoundecanoyl)vinblastine

A solution of 218 μl (1.69 mmol) of isobutyl chloroformate in 1 ml of ethyl acetate is added dropwise to a solution of 476 mg (1.69 mmol) of N-maleoyl-11-aminoundecanoic acid and 326 μl (2.8 mmol) of N-methylmorpholine in 3 ml of ethyl acetate cooled to 0° C. The mixture is stirred for 3 minutes at 0° C., and 433 mg (0.56 mmol) of O$^4$-deacetylvinblastine dissolved in 1 ml of ethyl acetate are then added while the temperature is kept at 0° C. The mixture is then allowed to return to room temperature and is stirred overnight.

The solution is filtered and the ethyl acetate phase evaporated to dryness under vacuum. The residue obtained is purified by chromatography on a silica column (elution: ethanol/ethyl acetate, 30:90). 240 mg of pure product are thereby obtained.

Yield: 41%,

NMR spectrum (CDCl$_3$, 360 MHz ppm):

Spectre RMN (CDCl$_3$, 360 MHz, ppm):

8 (1H, s, ind$^{16'}$NH); 7.5–7.13 (4H, m, H$^{11'}$H$^{12'}$H$^{13'}$H$^{14'}$); 6.68 (2H, s, maleimide db); 6.63 (1H, s, H$^{14}$); 6.10 (1H, s, H$^{17}$); 5.83 (1H, m, H$^7$); 5.48 (1H, s, H$^4$); 5.25 (1H, m, H$^6$); 3.95 (1H, m, H$^{17'}$); 3.80 (6H, s, OCH$_3$+C$^{23}$OOCH$_3$); 3.73 (1H, s, H$_2$); 3.6 (3H, s, C$^{18}$OOCH$_3$); 2.7 (3H, s, NCH$_3$); 1.28 (16H, broad peak, CH$_2$−); 0.88–0.8 (6H, t, CH$_3$−21−δCH$_3$−21′), IR spectrum (KBr, cm$^{-1}$) 3430, 3040, 2930, 2860, 1770, 1735, 1710, 1615, 1505, 1460, 1410, 1370, 1230–1250, 1000–1100.

Mass spectrum (DCI, isobutane): 1089, 1064, 1048, 1034, 1000, 990, 976, 960.

EXAMPLE 15

4-(N-maleoyl-12-aminododecanoyl)vinblastine

A solution of 307 μl (2.37 mmol) of isobutyl chloroformate in 1 ml of ethyl acetate is added dropwise to a solution of 699 mg (2.37 mmol) of N-maleoyl-12-aminododecanoic acid and 433 μl (3.95 mmol) of N-methylmorpholine in 4.2 ml of ethyl acetate cooled to 0° C.

The mixture is stirred for 3 minutes at 0° C. and 607 mg (0.79 mmol) of O$^4$-deacetylvinblastine dissolved in 1 ml of ethyl acetate is then added while the temperature is kept at 0° C. The mixture is then allowed to return to room temperature and is stirred overnight.

The solution is filtered and the ethyl acetate phase evaporated to dryness under vacuum. The residue obtained is purified by chromatography on a silica column (elution: ethanol/ethyl acetate, 30:90). 271 mg of pure product are thereby obtained.

Yield: 33%

NMR spectrum (CDCl$_3$, 360 MHz, ppm): 8 (1H, s, ind$^{16'}$NH); 7.5–7.10 (4H, m, H$^{11'}$H$^{12'}$H$^{13'}$H$^{14'}$); 6.65 (2H, s, maleimide db); 6.60 (1H, s, H$^{14}$); 6.08 (1H, s, H$^{17}$); 5.83 (1H, m, H$^7$); 5.48 (1H, s, H$^4$); 5.25 (1H, d, H$^6$); 3.95 (1H, m, H$^{17'}$); 3.78 (6H, s, −OCH$_3$+C$^{23}$OOCH$_3$); 3.73 (1H, s, H$^2$); 3.6 (3H, s, C$^{18'}$OOCH$_3$); 2.7 (3H, s, NCH$_3$); 1.25 (20H, m, −CH$_2$−); 0,9–0,8 (6H, t, CH$_3$−21+CH$_3$−21′)

IR spectrum (KBr, cm$^{-1}$): 3460, 3040, 2930, 2860, 1735, 1700, 1610, 1500, 1460, 1430, 1410, 1365, 1245, 1220.

Mass spectrum (DCI, isobutane): 1063, 1046 (M$^+$+1), 1037, 1028, 1016, 312, 117.

EXAMPLE 16

4-(N-maleoyl-L-alanyl)lysylvinblastine ethyl ester

A solution of 150 mg (0.163 mmol) of 4-(N-maleoyl-L-alanyl)vinblastine in 1 ml of ethanol is added dropwise to a solution of 40.26 mg (0.163 mmol) of lysine ethyl ester HCl and 150 μl (0.978 mmol) of triethylamine in 7.5 ml of absolute ethanol. The mixture is stirred overnight at room temperature and the solution then evaporated. The residue obtained is purified by chromatography on a silica column (elution: 14% MeOH/NH$_3$ in ether). 101.2 mg of pure product are thereby obtained.

Yield: 67%.

Mass spectrum (DCI, isobutane): 1,095 (M$^+$+2); 1,094 (M$^+$+1); 1,037; 921; 839; 769; 693; 615; 574; 532.

IR spectrum (KBr) cm$^{-1}$: 3,460; 2,940; 1,740; 1,710; 1,615; 1,500; 1,460; 1,430; 1,590; 1,250; 1,225; 1,120; 1,010; 735.

NMR spectrum (CDCl$_3$, 360 MHz, ppm): 8 (1H, NH, 16′); 7.5–7.1 (4H, H$^{11'}$, H$^{12'}$, H$^{13'}$, H$^{14'}$); 6,6 (1H, s, H$^{14}$); 6,08 (1H, s, H$^{17}$); 5,8 (1H, m, H$^7$); 5,45 (1H, s, H$^4$); 5,3 (1H, m, H$^6$); 4,8 (1H, m, CH*); 4,18 (2H, q, −OCH$_2$); 3,83 (3H, s, OCH$_3$); 3,78 (3H, s, OCH$_3$); 3,6 (3H, s, OMe); 2,68 (3H, s, NCH$_3$); 1,65 (3H, d, ala CH$_3$); 1,43 (2H, s); 1,28 (CH$_3$, OCH$_2$CH$_3$); 0,9–0,8 (6H, CH$_3$−21+CH$_3$−21′).

EXAMPLE 17

Coupling of 4-(N-maleoyl-L-alanyl)vinblastine with galactosylated human albumin (HAgal)

(V$_4$-Ala-Mal-HAg)

44 mg of 4-(N-maleoyl-L-alanyl)vinblastine are dissolved in 1 ml of dioxane. A solution of 50 mg of HAgal in 5 ml of 0.2M phosphate buffer pH 8.5 is prepared separately. The solution of 4-(N-maleoyl-L-alanyl)vinblastine is added to the solution of HAgal. The mixture is stirred at room temperature overnight and purified by gel filtration on Sephadex G-25 (2.6×96 cm) equilibrated to 0.9% strength NaCl solution pH 7.5. The excluded peak is collected (96 ml), concentrated by ultrafiltration and sterilized.

The protein content is measured by Lowry method and the alkaloid content is estimated by measuring the radioactivity. The conjugate obtained contains 13.5 mols of alkaloid per mol of galactosylated human albumin.

EXAMPLE 18

Coupling of 4-(N-maleoyl-6-aminocaproyl)vinblastine with galactosylated human albumin (HAgal)

($V_4$-$C_6$-Mal-HAg)

234 mg of 4-(N-maleoyl-6-aminocaproyl)vinblastine are dissolved in 1 ml of dioxane. A solution of 50 mg of HAgal in 5 ml of 0.2M phosphate buffer pH 8.5 is prepared separately. The solution of 4-(N-maleoyl-6-aminocaproyl)vinblastine vinblastine is added to the solution of HAgal. The mixture is stirred at room temperature overnight and then purified by gel filtration on Sephadex G-25 (2.6×96 cm) equilibrated to 0.9% strength NaCl solution pH 7.5. The excluded peak is collected (100 ml), concentrated by ultrafiltration and sterilized. The protein content is measured by the Lowry method and the alkaloid content estimated by measuring the radioactivity. The conjugate obtained contains 12.7 mols of alkaloid per mol of galactosylated human albumin.

EXAMPLE 19

Coupling of 4-(N-maleoyl-L-glutamyl)vinblastine γ-methyl ester with galatosylated human albumin (HAgal)

($V_4$-GluγME-Mal-HAg)

24 mg of 4-(N-maleoyl-L-glutamyl)vinblastine γ-methyl ester are dissolved in 1 ml of dioxane. A solution of 50 mg of HAgal in 5 ml of 0.2M phosphate buffer pH 8.5 is prepared separately. The solution of 4-(N-maleoyl-L-glutamyl)vinblastine γ-methyl ester is added to the solution of HAgal. The mixture is stirred at room temperature overnight and purified by gel filtration on Sephadex G-25 (26×96 cm) equilibrated to 0.9% strength NaCl solution pH 7.5. The excluded peak is collected (100 ml), concentrated by ultrafiltration and sterilized. Protein content is measured by the Lowry method and the alkaloid content estimated by measuring the radioactivity. The conjugate obtained contains 11.8 mols of alkaloid per mol of galactosylated albumin.

EXAMPLE 20

Coupling of 4-(N-maleoyl-L-isoleucyl)vinblastine with galactosylated human albumin (HAgal)

($V_4$-Ile-Mal-HAg)

250 mg of 4-(N-maleoyl-L-isoleucyl)vinblastine are dissolved in 20 ml of dioxane.

A solution of 591 mg of HAgal in 16.5 ml of 0.4M phosphate buffer pH 8.5 is prepared separately.

The solution of 4-(N-maleoyl-L-isoleucyl)vinblastine is added to the solution of HAgal. The mixture is stirred at room temperature overnight and purified by gel filtration on Sephadex G-25 (2.6×96 cm) equilibrated to 0.9% strength NaCl solution pH 7.5. The excluded peak is collected (180 ml), concentrated by ultrafiltration and sterilized.

The protein content is measured by the Lowry method and the alkaloid content is estimated by measuring the radioactivity.

The conjugate obtained contains 8.8 mols of alkaloid per mol of galactosylated human albumin.

EXAMPLE 21

Coupling of 4-(N-maleoyl-L-aspartyl)vinblastine α-benzyl ester with galactosylated human albumin (HAgal)

($V_4$-AspαBE-Mal-HAg)

105 mg of 4-(N-maleoyl-L-aspartyl)vinblastine α-benzyl ester are dissolved in 7.9 ml of dioxane.

A solution of 226 mg of HAgal in 6.3 ml of 0.4M phosphate buffer pH 8.5 is prepared separately.

The solution of 4-(N-maleoyl-L-aspartyl)vinblastine benzyl ester is added to the solution of HAgal. The mixture is stirred at room temperature overnight and purified by gel filtration on Sephadex G-25 (2.6×96 cm) equilibrated to 0.9% strength NaCl solution pH 7.5. The excluded peak is collected (60 ml), concentrated by ultrafiltration and sterilized.

The protein content is measured by the Lowry method and the alkaloid content estimated by measuring the radioactivity.

The conjugate obtained contains 5.7 mols of alkaloid per mol of galactosylated human albumin.

EXAMPLE 22

Coupling of 4-(N-maleoyl-11-aminoundecanoyl)vinblastine with galactosylated human albumin (HAgal)

($V_4$-$C_{11}$-Mal-HAg)

440 mg of 4-(N-maleoyl-11-aminoundecanoyl)vinblastine are dissolved in 46 ml of dioxane.

A solution of 969 mg of HAgal in 27 ml of 0.4M phosphate buffer pH 8.5 is prepared separately.

The solution of 4-(N-maleoyl-11-aminoundecanoyl)vinblastine is added to the solution of HAgal. The mixture stirred at 40° C. for 5 hours and purified by gel filtration on Trisacryl (5.6×50 cm) equilibrated to 0.9% strength NaCl solution pH 7.5. The excluded peak is collected (250 ml), concentrated by ultrafiltration and sterilized.

The protein content is measured by the Lowry method and the alkaloid content estimated by measuring the radioactivity.

The conjugate obtained contains 10.2 mols of alkaloid per mol of galactosylated human albumin.

EXAMPLE 23

Coupling of 4-(N-maleoyl-12-aminododecanoyl)vinblastine with galactosylated human albumin (HAgal)

($V_4$-$C_{12}$-Mal-HAg)

120 mg of 4-(N-maleoyl-12-aminododecanoyl)vinblastine are dissolved in 16 ml of dioxane.

A solution of 339 mg of HAgal in 9.4 ml of 0.4M phosphate buffer pH 8.5 is prepared separately.

The solution of 4-(N-maleoyl-12-aminododecanoyl)vinblastine is added to the solution of HAgal. The mixture is stirred at 40° C. for 6 hours and purified by gel filtration on Trisacryl (5.6×50 cm) equilibrated to 0.9% strength NaCl solution pH 7.5. The excluded peak (240 ml) is collected, concentrated by ultrafiltration and sterilized.

The protein content is measured by the Lowry method and the alkaloid content estimated by measuring the radioactivity. The conjugate obtained contains 9 mols of alkaloid per mol of galactosylated human albumin.

EXAMPLE 24

Coupling of 4-(N-Maleoyl)-L-alanyl vinblastine with non specific immunoglobulin (IgG)

($V_4$-AlaMal-IgG)

4 mg of 4-(N-Maleoyl)-L-alanyl vinblastine are dissolved in 193 μl of ethanol. On the other hand, a solution of 10 mg IgG (626 μl) in 357 μl phosphate buffer 0.4M at pH 8.5 and 447 μl water (7 mg prot/ml) is prepared. The solution of 4-(N-Maleoyl)-L-alanyl vinblastine is added to the IgG solution. The mixture is stirred at 35° C. during one night and purified by HPLC on a column (gel filtration) of Dupont de Nemours GF 450+250 equilibrated in a phosphate buffer 0.2M at pH 7.5.

The excluded peak is collected and the quantity is determined.

The protein content is measured by the Lowry Method and the alcaloid content is estimated by determination of the radioactivity. The obtained conjugate contains 6.6 moles alcaloid per mole immunoglobuline.

The compounds of the invention were subjected to a pharmacological study.

1. Sensitivity to lysosomal enzymes

The sensitivity of the conjugates to lysosomal enzymes was studied by incubation of these conjugates for 48 hours at 37° C. in the presence of 5 mM cystein, 40 mM acetate buffer and lysosomal enzymes.

After 48 hours' incubation, the undegraded proteins are precipitated, after adding 5 mg of serum albumin, with 2 volumes of acetonitrile.

After incubation of the samples at 4° C. for 40' and centrifugation at 3000 rpm for 40', the radioactivity of the supernatant is estimated by liquid scintillation counting of an aliquot portion. The soluble radioactivity is a measure of the digestion of the conjugate.

The percentage digestion values obtained are as follows:

$V_4$-Ala-Mal-HAg: 92%
$V_4$-$C_6$-Mal-HAg: 100%
$V_4$-Ile-Mal-HAg: 75%
$V_4$-$C_{11}$-Mal-HAg: 79%
$V_4$-$C_{12}$-Mal-HAg: 92%

2. Stability is serum

The stability of the conjugates in the presence of serum was studied by incubating the conjugate in the presence of 62% fetal calf serum at 37° C. for 48 hours.

After 48 hours' incubation, the undegraded proteins are precipitated by adding one volume of trichloroacetic acid (40% strength TCA). After incubation of the samples at 4° C. for one hour, the latter are centrifuged and the radioactivity of the supernatant is estimated by liquid scintillation counting of an aliquot portion.

The soluble radioactivity is a measure of the digestion of the conjugate.

The results show that the conjugates are stable during 48 hours.

3. Stability of acid pH

The stability of the conjugates at acid pH was studied by incubating the conjugate in the presence of 40 mM acetate buffer, pH 4.5, at 37° C. for 48 hours. The digestion is estimated by the TCA precipitation technique.

The results show that the conjugates are stable under these conditions.

4. Chemotherapeutic activity on leukemia P 388

The chemotherapeutic activity of the intermediate derivatives and the conjugates was assessed on leukemia P388 administered i.p. to female $BDF_1$ mice: $10^6$ tumor cells are inoculated i.p. on day 0. The conjugate is administered i.p. on day 1.

The ILS value represents the percentage survival time of the treated mice compared with that of untreated mice.

The mol ratio indicates the number of mols of alkaloid per mol of galactosylated human albumin.

The number of mice surviving at day 60 is shown, as well as the dose in mg/kg of the alkaloid and the protein.

3.1. Intermediate derivatives

| Product | Dose mg/kg/d | ILS % | Survivors at day 60 |
|---|---|---|---|
| VBL (vinblastine) | 3 | 77 | 0/10 |
| VCR (vincristine) | 2.7 | 64 | 0/11 |
| $V_4$—Ala—Mal (Example 9) | 25 | 100 | 0/7 |
|  | 50 | 127 | 0/7 |
|  | 75 | −70 | 0/6 |
| $V_4$—GluγME—Mal (Ex 11) | 50 | 88 | 0/10 |
|  | 100 | 111 | 0/10 |
| $V_4$—Ile—Mal (Example 12) | 50 | 148 | 0/7 |
|  | 100 | −79 | 0/7 |
| $V_4$—$C_6$—Mal (Example 10) | 25 | 102 | 0/8 |
|  | 50 | 218 | 1/7 |
|  | 100 | −83 | 0/7 |
| $V_4$—$C_{11}$—Mal (Example 14) | 50 | 37 | 1/7 |
|  | 100 | −19 | 1/5 |
| $V_4$—$C_{12}$—Mal (Example 15) | 25 | 185 | 1/5 |
|  | 50 | >633 | 6/8 |
|  | 100 | 7 | 1/7 |

3.2. Conjugates

| Product | Dose mg/kg/d Vinca | Protein | Mol ratio | ILS % | Survivors day 60 |
|---|---|---|---|---|---|
| VBL | 3 |  |  | 77 | 0/10 |
| VCR | 2.7 |  |  | 64 | 0/11 |
| $V_4$—Ala—Mal—HAg | 60 | 374–466 | 13.5–10.7 | 69 | 0/5 |
|  | 80 | 450 | 15 | 133 | 1/5 |
|  | 100 | 562 | 15 | 201 | 0/5 |
|  | 130 | 2766 | 6.6 | 175 | 1/3 |
|  | 150 | 3035 | 4.1 | 138 | 0/7 |
|  | 150 | 1276 | 9.8 | >552 | 3/5 |
|  | 150 | 913 | 13.7 | >574 | 3/5 |
| $V_4$—AspαBE—Mal—HAg | 60 | 768 | 5.7 | 47 | 0/5 |
| $V_4$—GluγME—Mal—HAg | 60 | 987 | 4.7 | 67 | 0/5 |
|  | 100 | 1645 | 4.7 | 75 | 0/5 |
|  | 150 | 2468 | 4.7 | 88 | 0/5 |

-continued

| Product | Dose mg/kg/d Vinca | Protein | Mol ratio | ILS % | Survivors day 60 |
|---|---|---|---|---|---|
| $V_4$—Ile—Mal—HAg | 60 | 545 | 8.8 | 51 | 0/5 |
| | 100 | 908 | 8.8 | 48 | 0/5 |
| | 150 | 1362 | 8.8 | 79 | 0/5 |
| $V_4$—$C_6$—Mal—HAg | 60 | 400 | 12 | 95 | 0/5 |
| | 150 | 995 | 12 | 137 | 1/5 |
| $V_4$—$C_{11}$—Mal—HAg | 60 | 378 | 11.8 | 147 | 1/5 |
| | 80 | 504 | 11.8 | 153 | 1/5 |
| | | 753 | 7.9 | | |
| | 90 | 658 | 10.2 | 227 | |
| | 100 | 630 | 11.8 | >606 | 3/5 |
| | 100 | 646 | 7.9 | 186 | 3/10 |
| | 150 | 945 | 11.8 | −45 | 0/5 |
| $V_4$—$C_{12}$—Mal—HAg | 90 | 741 | 9 | >769 | 5/5 |

We claim:

1. Conjugates of vinca alkaloid of the indole-dihydroindole type corresponding to the general formula:

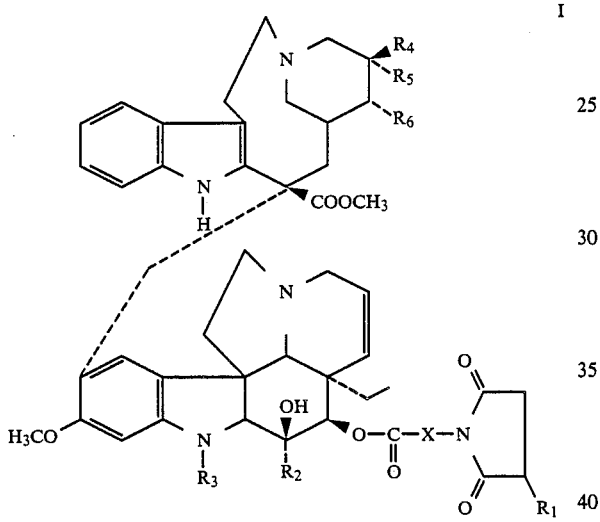

in which $R_1$ denotes a protein or a protein fragment obtained by digestion of a protein with a proteolytic enzyme, said group $R_1$ being bonded at the position shown via a sulfur atom of a thiol group or a nitrogen atom of an amino group;

$R_2$ is $COO(C_{1-3}$ alkyl), or $R_2$ is CO—$R_7$ where $R_7$ is $NH_2$, an amino acid esterifying group or a peptide esterifying group;

$R_3$ is H, $CH_3$ or CHO;

$R_6$ is H and one of $R_4$ and $R_5$ is then ethyl and the other is H or OH;

or $R_5$ and $R_6$ together form an oxirane ring with the carbon atoms to which they are attached and $R_4$ is ethyl; and, X denotes a linear alkylene chain of 1–12 carbon atoms, a branched alkylene chain of 2 to 5 carbon atoms, a cycloalkylene chain of 3 to 6 carbon atoms, the group RCH of natural amino acids

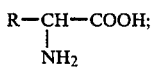

or a peptide chain fragment of the type —($X_1$)—NH—CO)$_n$—$X_1$— in which n=1, 2, 3 or 4 and $X_1$ is a linear alkylene chain of 1 to 12 carbon atoms, a branched alkylene chain of 2 to 5 carbon atoms, an ethyl phenyl radical or a phenyl radical, in its racemic form or in one of its optically active forms.

2. The conjugates as claimed in claim 1 in which $R_1$ is an immunoglobulin selected from the group consisting of:

Ig of goat or sheep immunized with carcinoembryonic antigen;

rabbit anti-LLA Ig;

various monkey anti-LLA, anti-LMA, anti-LLC, anti-LLLMC Ig's;

monoclonal Ig from mouse hybridomas secreting antibodies against human colorectal carcinoma;

monoclonal Ig from mouse hybridomas secreting antibodies against human melanoma;

monoclonal Ig from mouse hybridomas secreting antibodies which react with human leukemia cells;

monoclonal Ig from mouse hybridomas secreting antibodies which react with human neuroblastoma cells;

monoclonal Ig from mouse hybridomas secreting antibodies which react with human breast cancer antigens;

monoclonal Ig from mouse hybridomas secreting antibodies which react with human ovarian carcinoma cells;

monoclonal Ig from mouse hybridomas secreting antibodies which react with human osteosarcoma cells; and monoclonal Ig from mouse hybridomas secreting antibodies to lung cancer;

or an immunoglobulin fragment, namely Fab, Fab' or F(ab')$_2$ or monomeric IgM, obtained from an antibody by digestion with a proteolytic enzyme.

3. The conjugate as claimed in claim 1, in which the functional substitutents represented by X or $X_1$, are protected by protective groups.

4. The conjugate as claimed in claim 1, in which $R_1$ is bovine or human serum albumin, or fetuin or immunoglobulins.

5. The conjugate as claimed in claim 1, in which $R_1$ is galactosylated human albumin.

6. A process for preparing a conjugate of vinca alkaloid corresponding to the formula (I)

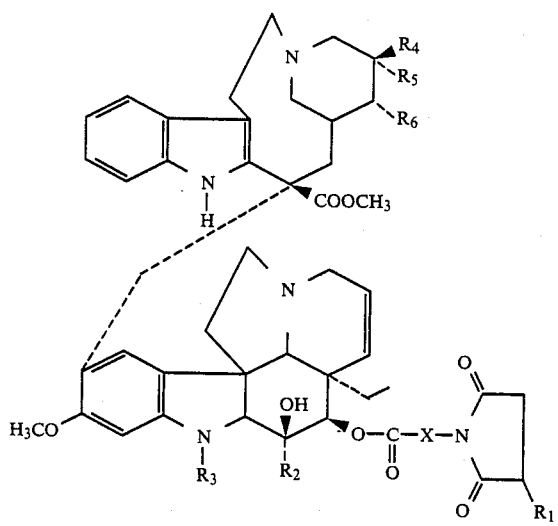

in which $R_1$, $R_2$, $R_3$, $R_4$, $R_5$, $R_6$ and X have the meanings stated in claim 1, wherein a maleoylamino acid or maleoyl peptide of formula

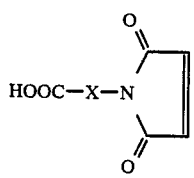

is esterified with the $C^4$-hydroxyl of a compound of general formula (II)

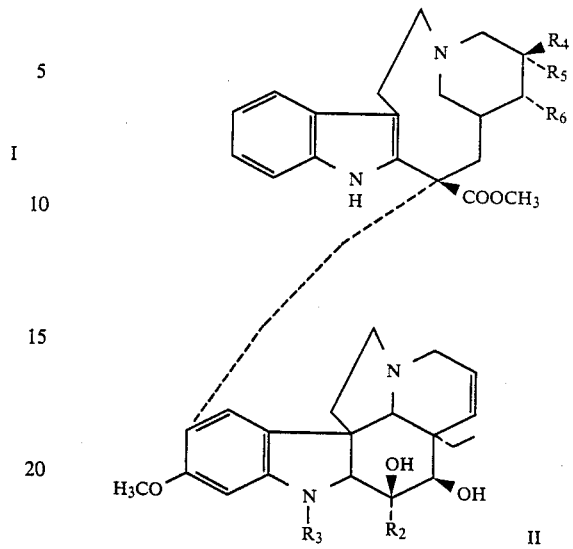

in which $R_2$, $R_3$, $R_4$, $R_5$, $R_6$ and X have the meanings stated, and wherein the intermediate product obtained is reacted in a Michael type addition reaction with a protein or a protein fragment obtained by digestion of a protein with a proteolytic enzyme.

7. The process as claimed in claim 6, wherein the esterification is accomplished by means of an alkyl chloroformate in the presence of an amine base in an organic solvent and wherein the intermediate compound obtained is isolated from the reaction medium and purified and wherein the Michael type addition reaction is accomplished in aqueous medium at a temperature of between 4° C. and 25° C. and a pH of 7.5 to 9.5.

8. A pharmaceutical composition containing, by way of active substance, the conjugate as claimed in claim 1, in combination with pharmaceutically acceptable carriers and excipients, according to a unit dose varying from 50 mg to several grams.

9. The pharmaceutical composition in claim 8 in the dissolved state in a pharmaceutically acceptable solvent.

10. The process as claimed in claim 7, wherein said alkyl chloroformate is selected from the group constituting of ethyl chloroformate and isobutyl chloroformate.

11. The process as claimed in claim 7, wherein said amino base is selected from the group constituting of triethylamine, N-methylpiperidine and N-methylmorpholine.

12. The process as claimed in claim 7, wherein said organic solvent is selected from the group constituting of ethyl acetate, tetrahydrofuran and methylene chloride.

13. A pharmaceutical composition as claimed in claim 8, wherein the pharmaceutically acceptable solvent is selected from the group constituting of physiological salines and solutions buffered by means of a phosphate buffer.

* * * * *